Figure 1:
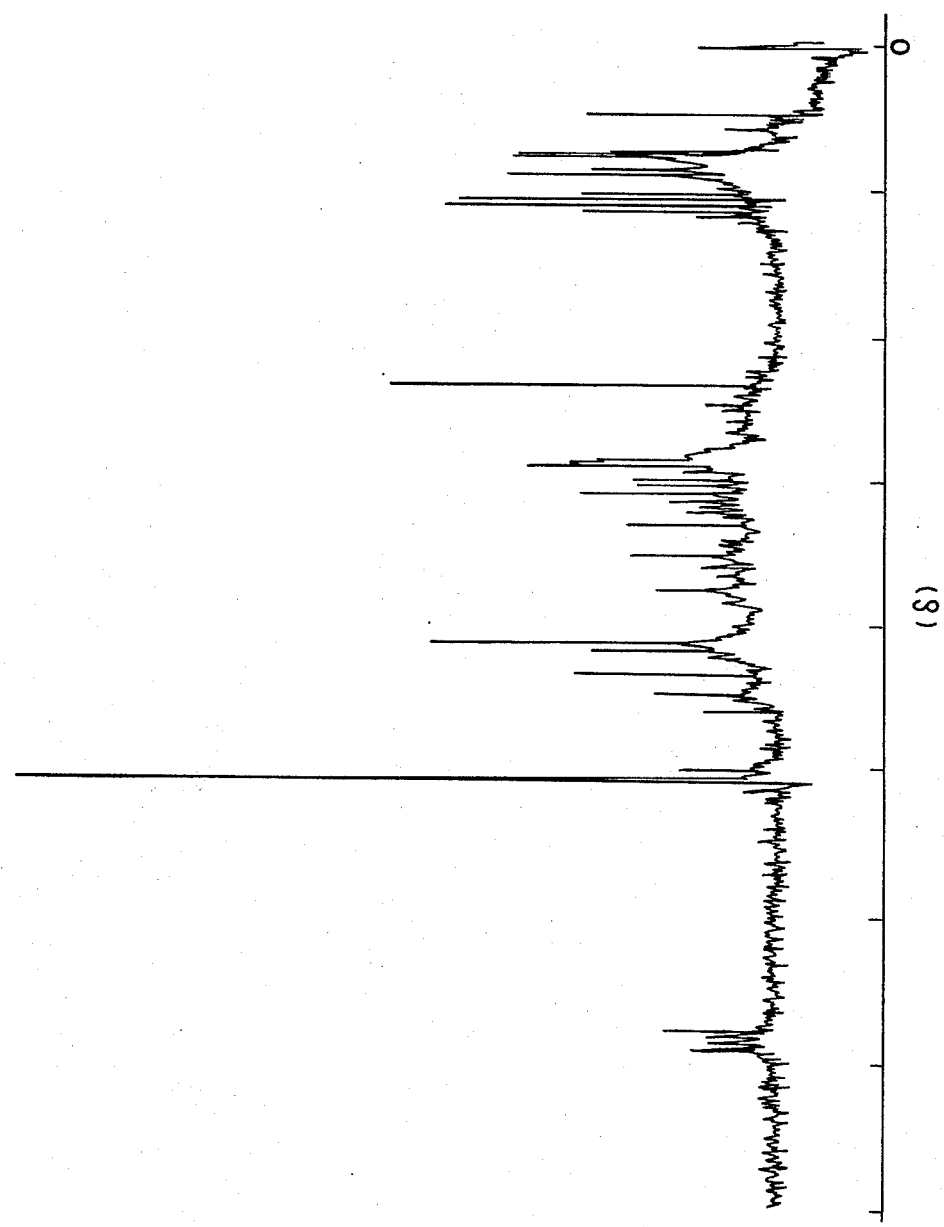

United States Patent [19]

Szent-Gyorgyi et al.

[11] 4,238,500
[45] Dec. 9, 1980

[54] CYCLIC DOUBLE HEMIACETALS OF ENEDIOL COMPOUNDS AND COMPOSITIONS AND METHODS FOR PREPARING AND USING SAME

[75] Inventors: Albert Szent-Gyorgyi, Woods Hole, Mass.; Gabor B. Fodor, Morgantown, W. Va.

[73] Assignee: National Foundation for Cancer Research, Bethesda, Md.

[21] Appl. No.: 27,692

[22] Filed: Apr. 6, 1979

[51] Int. Cl.³ .................. C07D 493/04; C07D 319/12; A61K 31/335; A61K 31/365
[52] U.S. Cl. ................................... 424/278; 424/279; 424/285; 260/340.6
[58] Field of Search ...................... 260/340.6; 424/279, 424/285, 278

[56] References Cited

U.S. PATENT DOCUMENTS

| | | | |
|---|---|---|---|
| 3,048,598 | 8/1962 | Croxall et al. | 260/340.6 |
| 3,555,006 | 6/1967 | Storfer | 536/114 |
| 3,847,948 | 11/1974 | Yamamoto et al. | 260/340.6 |
| 4,096,321 | 6/1978 | Weigele et al. | 260/340.9 |

OTHER PUBLICATIONS

Chem. Abst. 2261CS., vol. 86, 1977.
Freireich et al. Cancer Chemotherapy Report, No. 16, Feb. 1962, pp. 183-186.
Mihich, Cancer Research, vol. 23, Sep. 1963, pp. 1375-1389.
Alan Saito et al., Biochem. Biophys. Acta 103 (1965), pp. 174-179.

*Primary Examiner*—John D. Randolph
*Assistant Examiner*—Jane T. Fan
*Attorney, Agent, or Firm*—Fidelman, Wolffe & Waldron

[57] ABSTRACT

Novel chemical compounds of the general formulae:

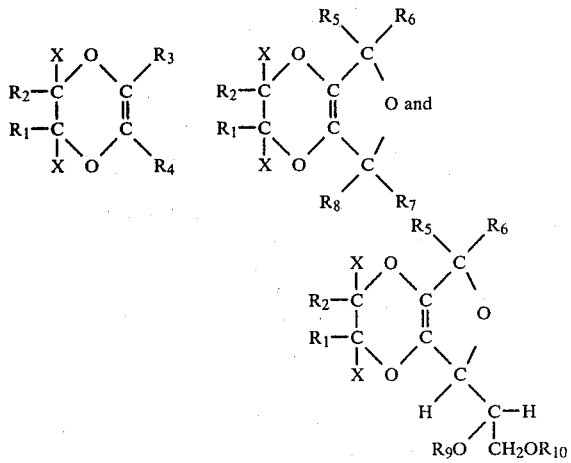

wherein $R_1$ and $R_2$ are hydrogen, alkyl, cycloalkyl, aryl or arylalkyl, wherein $R_3$ through $R_{10}$ are hydrogen, alkyl, or aryl, wherein $R_5$ and $R_6$ together may form =O, and wherein X is hydroxy. The compounds are prepared by mixing specified amounts of a dialdehyde, α-keto-aldehyde, or diketone, such as methylglyoxal or a related compound, and an enediol, such as L-ascorbic acid or a compound that can be converted into an enediol, such as an acyloin, and allowing same to react under a nitrogen atmosphere in the presence of a noninterfering solvent.

Compositions containing these novel compounds exhibit cytostatic, hypotensive and analgesic properties and are useful in the treatment of cancer in animals and humans.

10 Claims, 3 Drawing Figures

CYCLIC DOUBLE HEMIACETALS OF ENEDIOL COMPOUNDS AND COMPOSITIONS AND METHODS FOR PREPARING AND USING SAME

CROSS-REFERENCE TO A RELATED APPLICATION

This application is related to copending application Ser. No. 917,327 of Szent-Györgyi and Fodor, filed June 20, 1978, which is incorporated herein by reference.

BACKGROUND OF THE INVENTION

The present invention relates generally to novel chemical compounds and compositions, a process for preparing them, and use of these compounds and compositions as cytostatic, hypotensive and analgesic agents or for therapies involving all three properties.

Briefly, the compositions are prepared by mixing a specified part of a dialdehyde, α-keto-aldehyde or diketone with one part of an enediol or acyloin compound and allowing the mixture to react for prolonged time at room temperature. Following purification and sterilization, the composition is administered to animals harboring cancer cells. After administration, the cancer tissue is relieved of pressure by edema and further tumor development is arrested. Patients also experience a general loss of pain and a decrease in blood pressure.

For many years scientists have searched for an effective treatment for all types of cancer. Despite a great deal of interest and many important discoveries, these efforts have yet to make a major breakthrough in the cure or treatment of cancer.

According to A. Szent-Györgyi's bioelectronic theory of protein interactions (Szent-Györgyi, A., *Electronic Biology and Cancer*, M. Dekker, New York, 1976), methylglyoxal may play an important role in controlling cell division by virtue of its properties as a powerful electron acceptor. It interacts with proteins by means of its aldehydic carbonyl by attacking the primary amino groups of proteins. Independent of whether this theory proves in fact to be true, such regulation of cell division by methylglyoxal may be useful in the development of effective chemotherapeutic agents. However, methylglyoxal and related compounds are extremely labile in vivo due to the action of a glyoxalase enzyme system which converts it to D-lactic acid in the presence of reduced gluthathione. Therefore any in vivo test of methylglyoxal for its effect on cell division would prove negative because of the action of glyoxalase.

Szent-Györgyi extends his bioelectronic theory to explain cancer as a disturbance of the electronic configuration of proteins in cancer cells. (Szent-Guörgyi, *The Living State and Cancer*, in press). Briefly stated, he speculates that methylglyoxal and related compounds re-establish the proper protein configuration and cause cancer cells to revert from the abnormal state to proliferation to the normal 'resting condition'.

The use of a composition derived from methylglyoxal for the treatment of various cancers has been studied by Freireich, et al. (Cancer Chemotherapy Reports, Vol. 16, pp. 183–186, 1962). They reported clinical studies of methylglyoxal bis(guanylhydrazone) in patients with acute myelocytic leukemia and observed a complete remission frequency of 69% in 13 patients, leaving no doubt concerning its antitumor activity, particularly, they point out, when it is recalled that all then-current therapy could give only 13% complete remissions.

Additionally, in U.S. Pat. No. 2,893,912, Musser and Underwood present data to show that certain cyclic glyoxal compounds, e.g., cyclohexylglyoxal, benzylglyoxal, etc., have antiviral activity. In view of the current evidence that some forms of cancer are correlated with the occurrence of viral chromosomes in cancer cells, one may speculate that these compounds have potential in the prevention, cure and treatment of viral disease, including some forms of cancer.

U.S. Pat. No. 2,927,054 discloses the condensation of certain sugars, e.g., glucose, mannose, fructose, etc., with an aldehyde or ketone to form cyclic acetals of the sugar. The mechanism apparently involves the elimination of water by union of the oxygen of the carbonyl group of the aldehyde or ketone and the hydrogen from each of two hydroxyl groups of the sugar. This condensation reaction proceeds upon heating the mixture to the boiling point of the aldehyde in the presence of an acid acetalization catalyst, conditions favoring the open chain form of the sugar. The two adjacent carbon atoms of the cyclic acetal ring are adjacent carbons of the aliphatic chain of the sugar molecule. Several of such cyclic acetal rings may be formed on the same sugar molecule, forming poly-(cyclic acetals).

OBJECTS OF THE INVENTION

An object of the present invention is to provide novel compounds having cytostatic, hypotensive and analgesic activity.

Another object of this invention is to provide compositions effective in the treatment of cancer and hypertension, and in the relief of pain, and methods for the application of such compositions.

An additional object of the present invention is to provide compositions having the activities noted above, as well as other utilities as antitumor agents in animals and humans.

Still another object is to provide a process for preparing the novel compounds discussed herein.

A still further object of this invention is to perform the reaction of the dialdehydes, α-keto-aldehydes, or diketones and acyloin or enediol compounds of the invention in aqueous media in the presence of a non-interfering cosolvent.

Other objects, advantages and novel features of the present invention will become apparent from the following detailed discussion which includes reference to the following figures:

FIG. 1 presents a carbon magnetic resonance spectrum (CMR) of the products of the reaction between L-ascorbic acid and methylglyoxal.

Figure 2:
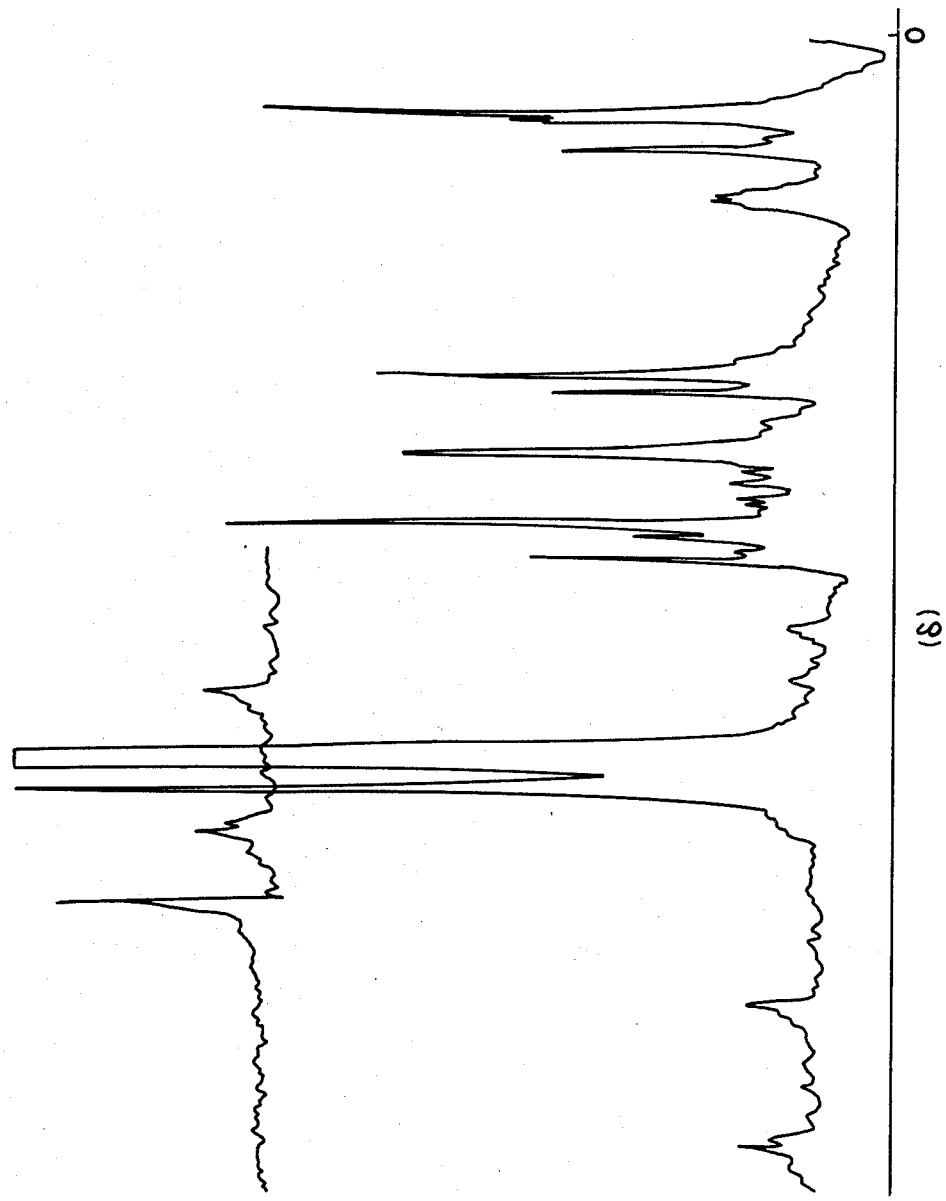

FIG. 2 presents a CMR of the products of the reaction between L-ascorbic acid and phenylglyoxal hydrate.

Figure 3:
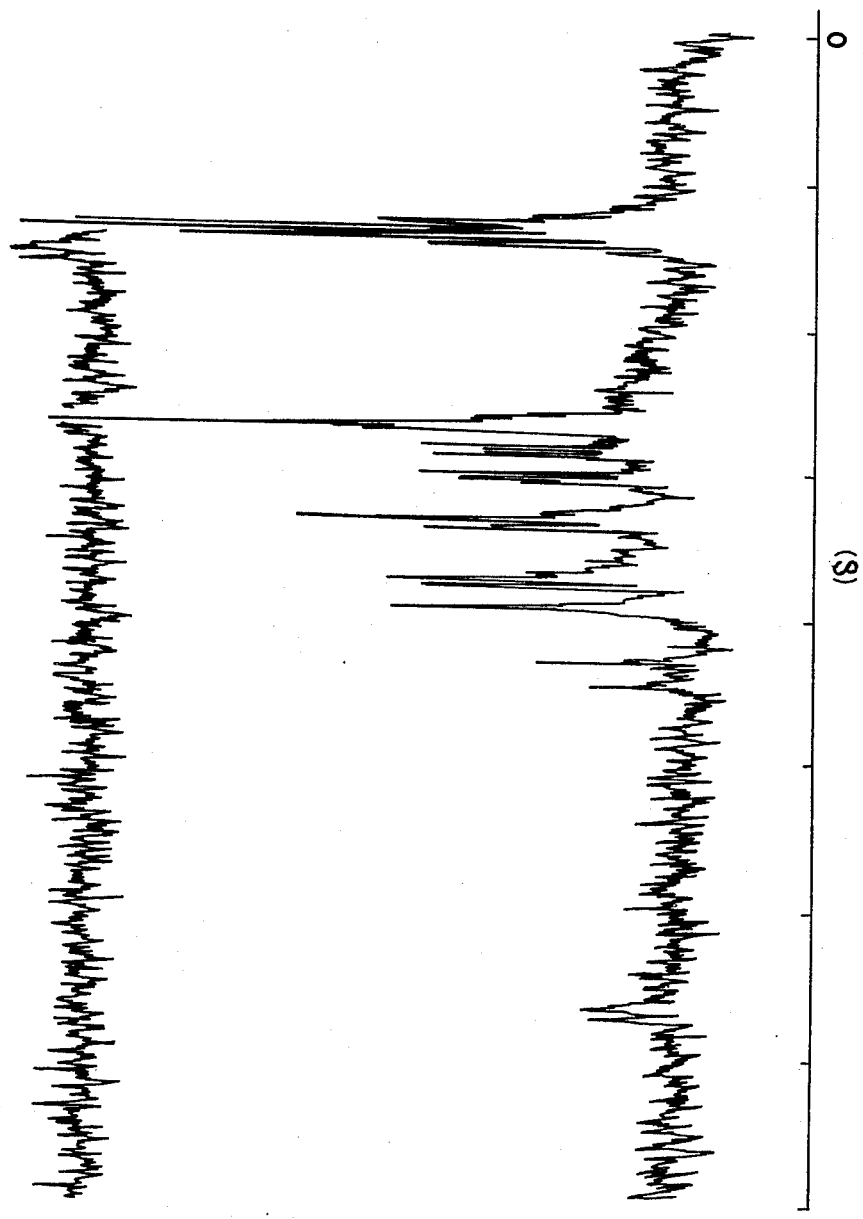

FIG. 3 presents a CMR of the products of the reaction between L-ascorbic acid and glyoxal.

DESCRIPTION OF THE INVENTION

The novel compounds of the instant invention are produced by mixing the required amounts of a dialdehyde, α-keto-aldehyde or diketone of the general formula

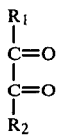

wherein $R_1$ and $R_2$ are hydrogen, alkyl, cycloalkyl, aryl, or arylalkyl and an acyloin or enediol compound of the general formula

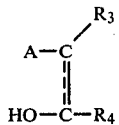

wherein A may be —OH or ═O, wherein══represents a double bond when A is —OH and a single bond when A is ═O, wherein $R_3$ and $R_4$ are hydrogen, alkyl, or aryl, or wherein $R_3$ and $R_4$ of the enediol reactant together form

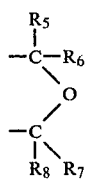

wherein $R_5$ through $R_8$ are hydrogen, alkyl, or aryl, wherein $R_5$ and $R_6$ together may form ═O, wherein $R_8$ may be

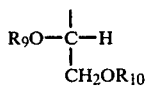

and wherein $R_9$ and $R_{10}$ are hydrogen, alkyl or aryl, and allowing them to react under a nitrogen atmosphere at about room temperature in aqueous media with a water-soluble cosolvent.

The novel cyclic double hemiacetals produced by the above-described process include

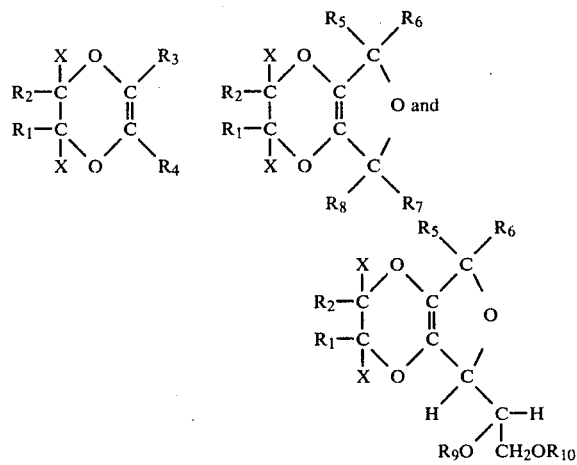

wherein $R_1$ and $R_2$ are hydrogen, alkyl, cycloalkyl, aryl, or arylalkyl, wherein X is hydroxy, wherein $R_5$ and $R_6$ together may form ═O, and wherein $R_3$ through $R_{10}$ are hydrogen, alkyl or aryl.

The novel cyclic hemiacetals of the instant invention also include the cases wherein $R_3$ and $R_4$ together form

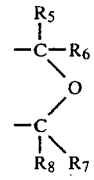

wherein $R_5$, $R_6$, $R_7$ and $R_8$ are hydrogen, alkyl or aryl and wherein $R_5$ and $R_6$ together may form ═O.

Additional products of the invention include cases wherein $R_5$ and $R_6$ above together form ═O, and wherein $R_8$ above is

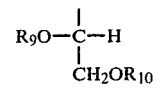

wherein $R_9$ and $R_{10}$ are hydrogen, alkyl or aryl.

The present invention differs from the invention of copending application Ser. No. 917,327, referred to above, with regard to the novel compounds and the method for making them. More specifically, the compounds of the instant application contain cyclic hemiacetal rings having six members, whereas the full acetal compounds of Ser. No. 917,327 have five-membered rings. Additionally, the process of making the compounds of the present invention includes reaction in aqueous media in the presence of a non-interfering cosolvent, such as, for example, tetra hydrofuran, dioxane or the like. In the process of preparing the compounds of Ser. No. 917,327 no cosolvents are present in the aqueous media of the reaction.

DETAILED EMBODIMENT

In the case where the reactants are either methylglyoxal, glyoxal or phenylglyoxal hydrate and L-ascorbic acid, reaction is indicated by a decrease in the reducing character of L-ascorbic acid toward iodine to 15, 0, and 25 percent, respectively, of the original values. The purified reaction products are obtained by evaporation in vacuo followed by washing with a solvent or solvents, column chromatography, and freeze-drying.

Methylglyoxal, glyoxal, and phenylglyoxal hydrate may be obtained commercially or purified as necessary.

Carbon magnetic resonance (CMR) spectra in the carbonyl region indicates a number of different lactone carbonyl absorptions (FIGS. 1, 2, and 3).

As far as the chemical characteristics of aforesaid compounds are concerned, gas chromatographic-mass spectral analysis of the reaction of the cyclic double hemiacetals of methyl-glyoxal, glyoxal, and phenylglyoxal hydrate and L-ascorbic acid with silylating agents, such as N,O-bis-(trimethylsilyl) /trifluoroacetamide, indicated cleavage to tetra-O-bis trimethyl silyl ascorbate in all cases (Fales, Fodor and Butterick, unpublished results). This clearly indicates (a) reversibility of the reaction, (b) no structural change in L-ascorbic acid (c) that the trimethylsilylating agent acted as a trapping agent for L-ascorbic acid. Furthermore, semicarbazide gave pyruvic aldehyde semicarbazone and, on the other hand, oxidative cleavage with sodium periodate of sodium bicarbonate-buffered samples resulted in consumption of two equivalents of periodate, corresponding to 2 vicinal diol groupings per molecule.

From this data, one may infer that the enolic hydroxyls (at positions 2 and 3) of L-ascorbic acid reacted with the aldehyde carbonyl of methylglyoxal, glyoxal, and phenyl-glyoxal hydrate as well as with their ketone carbonyl groups to yield a series of cyclic double hemiacetals, which may be to a small extent in tautomeric equilibrium with the open chain hemiacetal in solution.

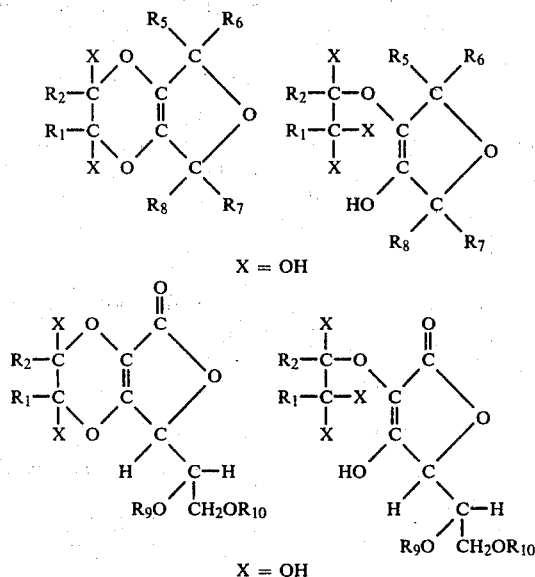

Detailed representative analytical data sheets for the methylglyoxal, glyoxal, and phenylglyoxal hydrate compounds are included in Examples 6, 7, and 8. These findings are inconsistent with a physical mixture of L-ascorbic acid and methylglyoxal which would require at least three moles of $NaIO_4$ to be consumed. It should be noted that L-ascorbic acid itself uses 2.21 equivalents $NaIO_4$, while methylglyoxal consumes 1.29 mole.

Over-oxidation to a limited extent by periodate may explain the consumption of more than 2 or 1 equivalents of $NaIO_4$ as may be expected for L-ascorbic acid and methylglyoxal, respectively.

EXAMPLE 1

A one-necked two liter round bottom flask covered with aluminum foil was charged with 68 g (0.386 moles) of L-ascorbic acid. To this one liter of tetrahydrofuran (analytical grade, Mallinckrodt),* 340 ml (nitrogen purged) of distilled water and 268 g of methylglyoxal 40% aqueous solution (Aldrich, #17, 733-4), were added in turn. The flask was stoppered and stirred at ambient temperature (23°) for 4 days.
* stripped of peroxides by stir-batching with neutral alumina and suction filtration.

0.1 ml aliquots were taken, diluted with 1 ml $H_2O$ and titrated with 0.1 M solution iodine in tetrahydrofuran (THF). When iodine reduction reached the asymptote (0.26 ml), the reaction was considered complete.

The solvent from the reaction mixture was evaporated on a rotary evaporator at 15 mm–20 mm (water bath$\geq 35°$), a vacuum pump$\geq 0.4$ mm, and finally a freeze drier at $200\mu$. The resulting yellow syrup was freeze-dried for 3 days at $10\mu$. The yellow foam obtained was treated with a solution of 400 ml anhydrous ethyl acetate and 1 liter anhydrous benzene* and cooled to $-15°$. After 2 days, the solution was decanted from the solid. The solid material was freeze-dried at $15\mu$ for 3 days. The resulting white puffy solid was further purified (when necessary to remove the L-ascorbic acid) by dissolution in 800 ml anhydrous ethyl acetate/anhydrous cyclohexane* (1:1), cooling to 0° for 1 day, suction filtration of the solid, evaporation of the filtrate for 15–20 min. (water bath 35°) and freeze drying for one day.
** dried over $P_2O_5$ at ambient temperature for 12 hours and distilling at atmospheric pressure protected from moisture.
*** dried over sodium at ambient temperature for 12 hours and distilling at atmospheric pressure protected from moisture.

In either of the two cases, the 5–10% L-ascorbic acid contaminated preparation or the L-ascorbic acid-free methylglyoxal-ascorbic acid compound, complexed and matrix-bound solvents were removed by cooling to dry ice or liquid nitrogen temperature and freeze-drying ($15\mu$) six times over 3 days.

Based on L-ascorbic acid the yield of (5–10% ascorbic acid)—methylglyoxal-ascorbic acid compound was 95–100 g, m.p. 58°–62°. The yield of L-ascorbic acid free methyl glyoxal-ascorbic acid compound was 80–85 g (90–96%), m.p. 52–54.

EXAMPLE 2

15.2 grams (0.10 mole) of phenylglyoxal monohydrate were added to a solution of 17.6 grams (0.10 mole) of L-ascorbic acid dissolved in a mixture of 500 ml oxygen-free distilled water and 500 ml tetrahydrofuran (see Example 1) in a nitrogen atmosphere. The reaction was stirred under nitrogen in the dark for 4 days at ambient temperature. When an aliquot was titrated as in Example 1, the reaction had consumed 75% of the inital L-ascorbic acid and was considered complete. The reaction was quenched by removal of water on a freeze drier and the residue weighing 30 grams was subjected to further purification on a cellulose column.

EXAMPLE 3

A solution of 11.6 g (0.1 mole) of the enediol v-lactone of dihydroxy acetoacetic acid ($C_4H_4O_4$), m.p. 153°, prepared according to Micheel and Jung (Chem. Ber., 66B, 129 (1933)), was dissolved in a mixture of 100 ml, tetrahydrofuran and 56 ml water under nitrogen. Thereupon 36 ml of a 40% aqueous solution of methylglyoxal (0.2 mole) was added and the reaction followed by iodine titration of withdrawn samples. After the reaction was practically complete, the reaction mixture of the hemiacetal hemiketal of the enediol lactone (5,6-bis-norascorbic acid) was evaporated on a freeze-dryer at $15\mu$ for three days and subjected to purification by passing through a cellulose column. The yield was 18 g (95%) after chromatography.

Compositions useful in the treatment of pain, hypertension and cancer may include the known pharmaceutical carriers, as, for example, 0.9 percent saline or water. A preferred composition comprises a compound of the invention dissolved in about 10 to 10,000 weight percent, based on the total weight of said compound, of 0.9 percent saline or water.

The reactions of Examples 1 to 3 were performed in aqueous media in the presence of a non-interfering cosolvent (THF), but the presence of a cosolvent is not necessary for the reaction to occur. The six-membered ring hemiacetal compounds of the invention are produced in aqueous media along with the five-membered ring acetal compounds of Ser. No. 917,321, referred to above. It is believed that the cosolvent directs the reaction to favor production of the hemiacetal over the acetal compound, but the extent to which the cosolvent alters the equilibrium levels is, at present, unknown.

EXAMPLE 4

100 mg of the compounds of Examples 2 and 3 were treated with 2 ml of N,O-bis(trimethylsilyl)trifluoroacetamide (Pierce) at ambient temperature for 4-7 days and the reagent removed under high vacuum. The remaining material was dried at 10–15μ for 24 hours. A suitable anhydrous organic solvent, such as benzene, was introduced to form a solution of sufficient concentration for gas chromatographic analysis prior to gas chromatographic-mass spectral analysis.

EXAMPLE 5

Periodate oxidation of acetals and cyclic double hemiacetals of L-ascorbic acid

Compounds have been treated as follows. Firstly the compounds were dried to uniform weight on a freeze dryer. All oxidations and titrations were performed under nitrogen. Aliquots of 500 ml of a 0.020 N solution of the compounds were treated with approximately 10.0 ml of a saturated sodium bicarbonate solution (yielding a pH=7.20) and treated with exactly 20.0 ml of sodium arsenite solution (0.085 N). A solution of sodium periodate (0.040 N), 5.00 ml, was then added followed by approximately 1.50 ml 20% potassium iodide solution. The pH was still 7.20. Under nitrogen in subdued light, the oxidation was left for 15 minutes when the excess sodium arsenite was treated with 0.070 N iodine solution until just yellow (or where starch was used as indicator, the first persistent blue color appeared). A blank was used to correct for the volume of iodine used. In contrast with the five-membered ring containing full acetals described in patent application Ser. No. 917,327, referred to above, that consume about 1 mole of sodium periodate, the double hemiacetals of the present invention consume over 2 moles.

| Compound | USED (mole) | FOUND (mole) | Equivalents of periodate used |
|---|---|---|---|
| methylglyoxal L-ascorbic acid | .065 | .084 | 1.29 |
| (1 eq. methylglyoxal added) | .059 | .131 | 2.21 |
| L-ascorbic acid | .140 | .323 | 2.21 |
| L-ascorbic acid-methylglyoxal compound | .074 | .178 | 2.38 |
| glyoxal compound | .200 | .408 | 2.04 |
| L-ascorbic acid-crotonaldehyde compound | .195 | .267 | 1.36 |
| L-ascorbic acid-maleic aldehyde compound | .153 | .190 | 1.24 |
| mannitol | .039 | .226 | 1.15 |

Determination of formate and acetate in oxidation of ascorbic acid-methylglyoxal compound.

The periodate oxidation described above was performed at ten times the scale, with a 15 minute reaction time, and excess sodium borohydride added to quench the reaction. The reaction was acidified to pH 6 with dilute sulfuric acid (2N). Upon vacuum distillation and trapping of the acids, the distillate was basified with sodium carbonate and the water removed entirely on a freeze drier. A proton magnetic resonance spectrum of the freeze dried material was then taken and resonances at 1.90 ppm and 8.41 ppm ascribed to acetate ($CH_3$) and formate ($CH$), respectively, were observed (relative to DDS as internal standard). This finding is consistent with alkali hydrolysis of the enol acetate-formate and the reduction of periodate and iodate on the one hand, and of the resulting formaldehyde and $C_5$-aldehyde on the other.

A small portion of the freeze dried basified solution was dissolved in the minimum amount of water and neutralized with hydrochloric acid. 2-Benzyl-2-thiopseudourea hydrochloride was added and the S-benzyl thiuronium acetate and formate respectively, precipitated on freezing and thawing.

EXAMPLE 7

Methylglyoxal-ascorbic acid compound (prepared as in Example 1). Analytical Data $[\alpha]_D^{22} = 11.0°(C, 1.82)$ —20 mg sample in 0.1 ml $H_2O$ and 1 ml THF
PERKIN ELMER MODEL 141-2 mm path length cell
UV (ethyl acetate):δ246 (logε=2.99); 250 (2.92); 255 (2.76); 257 (2.76); 265–280 (2.64); 308 (2.34).
JASCO MODEL ORD/UV-5
IR (film): 3450, 1775, 1645 $cm^{-1}$
PERKIN ELMER 137
NMR ($CD_3COCD_3$, TMS) δ2.45–2.59 (5 $CH_3$'s), 4.52–4.66 ($CH_2O$, $CHO$, $C_2$—$CH$—O) obscurred by O$H$'s: 3.00–6.00, 5.25–5.28 ($O_2CH$'s)
VARIAN CFT 20
CMR ($CD_3COCD_3$, TMS): (18.00, 19.50, 19.89, 20.28, 22.35 (5 $CH_3$'s); 170.31, 171.14, 171.98, 172.10, 173.45 (O$C$OC=C)
VARIAN CFT 20
MICROANALYSIS (GALBRAITH LABORATORIES, TENN. USA) Analysis Calculated for $C_9H_{12}O_8$: C, 43.55; H, 4.84; O, 51.61. Found: C, 43.87; H, 6.14(!); O, 51.25.
OSMOMETRIC MOLECULAR WEIGHT (GALBRAITH) Calculated Molecular weight 248. Found (ethyl acetate) 250.
Melting point: 58°–62° (ascorbic acid present) 52°–54°, (ascorbic acid free).

EXAMPLE 8

Glyoxal-ascorbic acid compound (prepared as in Example 2, 0.1 mole of glyoxal).

Analytical Data $[\alpha]_D^{22} = 8.2(C, 1.82)$

—20 mg sample in 0.1 ml $H_2O$ and 1 ml THF

PERKIN ELMER MODEL 141-2 mm path length cell
UV (ethyl acetate): 246 (log$\epsilon$=3.95); 275 (2.64); 285 (2.34).
JASCO MODEL ORD/UV-5
IR (film): 3500–3200, 2950, 2880, 1775, 1690, 1645 cm$^{-1}$
CARY 14
NMR (CD$_3$COCD$_3$, TMS): $\delta$4.54, 4.59 and (C$\underline{H}_2$O, C$\underline{H}$O, C$_2$—C$\underline{H}$—O), 4.63, 4.94, 5.24 (O$_2$C$\underline{H}$)
VARIAN CFT 20
CMR (CD$_3$COCD$_3$, TMS): $\delta$55.0–99.0 (C$\underline{H}$, C$\underline{H}_2$), 173–174 (O$\underline{C}$=O)
VARIAN CFT 20
MICROANALYSIS (GALBRAITH LABORATORIES, TENN. USA) Analysis
Calculated for C$_8$H$_{10}$O$_8$: C, 41.03; H, 4.30; O, 54.57. Found: C, 41.28; H, 4.53; O, 54.70. Melting Point: 62°–66°.

EXAMPLE 9

Phenylglyoxal-ascorbic acid compound (prepared as in Example 2).

Analytical Data $[\alpha]_D^{22}$=11.8(C,1.82)

—20 mg sample in 0.1 ml H$_2$O and 1 ml THF
PERKIN ELMER MODEL 141-2 mm path length cell
UV (ethyl acetate): 248 (log=3.04)
JASCO MODEL ORD/UV-5
IR (film): 3450, 3000, 2900, 1790, 1700 cm$^{-1}$
CARY 14
NMR (CD$_3$COCD$_3$, TMS): $\delta$55.0–99.0 (C$\underline{H}$, C$\underline{H}_2$); 140–150 C$_6$H$_5$); 171–175 (O$\underline{C}$-O)
VARIAN CFT 20
MICROANALYSIS (GALBRAITH LABORATORIES, TENN. USA) Analysis
Calculated for C$_{14}$H$_{14}$O$_7$; C, 57.14; H, 4.80; O, 38.06. Found: C, 57.30; H, 4.93; O, 37.90. Melting Point: 70°–72°.

EXAMPLE 10

Purified methylglyoxal-ascorbic acid compound was tested in mice by single intraperitoneal (i.p.) injection and gaven an LD$_{50}$ in excess of 5 g/kg.

EXAMPLE 11

In the experiments with methylglyoxal-ascorbic acid compound, rats were anesthetized with 25% urethane i.p. and the jugular vein and carotid artery were cannulated. The compound was given intravenously (i.v.) and blood pressure was measured with a transducer attached to the corotid cannula. The results showed that the methylglyoxal-ascorbic acid compound produced a fall in both systolic and diastolic pressures within 10 minutes of commencing infusion of 500 mg/kg during a 15 minute infusion period. Pulse injection of the compound produced a transient fall in blood pressure followed by a reflex rise, bradycardia, and a slow subsequent fall of pressure below control values. It appears from these results that the methylglyoxal-ascorbic acid compound has a hypotensive effect at relatively high doses.

EXAMPLE 12

Effects on liver and kidney function

Rats were treated i.p. with the methylgloxal-ascorbic acid compound (500 mg/kg) versus an equivalent volume of saline (0.85% w/v) to test for significant damage to liver and kidney. No changes indicative of liver injury were seen, monitoring serum lactate dehydrogenase, sorbitol dehydrogenase, glutamate-oxaloacetate transaminase. The conclusions from these preliminary studies indicate that liver damage is not a significant feature with the doses of methylglyoxal-ascorbic acid compound used. The compound did produce a slightly more acidic urine than found in controls.

EXAMPLE 13

Effects on pain receptors

Guinea pig ileum was stimulated coaxially six times per minute and the effects of methylglyoxal, methylglyoxal-ascorbic acid compound and L-ascorbic acid on the twitch height and on contracture were measured and compared to the established effects of morphine.

Morphine gave a 50% reduction in twitch height at 8.5 mM; the corresponding ED$_{50}$ for methylglyoxal-ascorbic acid was 9–20 mM, for methylglyoxal, 8 mM; and for L-ascorbic acid; 32 mM. No further inhibition of twitch height occurred with increased concentrations.

These results show that the morphine/methylglyoxal-ascorbic acid compound ratio of efficiency is approximately 10$^6$.

EXAMPLE 14

Effects on Inflammation

In one series of tests, rats were treated i.v. with trypan blue and then the increased capillary permeability produced by intradermal injection of serotonin (0.05 $\mu$g) or histamine (1 $\mu$g) was measured.

Methylglyoxal-ascorbic acid compound (200 mg/kg) or L-ascorbic acid (100 mg/kg) were injected i.p. 30 minutes before the testing of capillary permeability, and stain diffusion was observed for 20–30 minutes after serotonin or histamine. No effect of methylglyoxal-ascorbic acid compound or L-ascorbic acid could be found in this system.

In other experiments, edema of the rat paw was produced by intradermal injection of carrageenan (0.1 ml of 1% solution in saline). The volume of the rat paw was measured using a differential volumometer (U. Basile, Milan, Italy) methylglyoxal-ascorbic acid compound (200 mg/kg), L-ascorbic acid (199 mg/kg) or indomethacin (3 mg/kg) were injected i.p. (methylglyoxal-ascorbic acid compound and L-ascorbic acid) or given per os (indomethacin) 60 minutes prior to the carrogeenan. Both methylglyoxal-ascorbic acid compound and L-ascorbic acid were somewhat anti-inflammatory in this respect but they were far less active than indomethacin (ratio of effectiveness approximately 200).

EXAMPLE 15

Tumor studies

In rat studies, methylglyoxal-ascorbic acid compound (500 mg/kg, once daily, i.p.) inhibited Ehrlich carcinoma and Sarcoma 180 in both solid (approximately 36%) and ascitic (approximately 96%) forms. Methylglyoxal-ascorbic acid compound (250 mg/kg, twice daily, i.p.) inhibited the ascitic forms (approximately 90%) but not the solid forms of these tumors.

The mode of action of the compounds of the invention with respect to cytostatic, hypotensive and pain relieving activities is, at this point, unclear. However the empirical observation that cells stop proliferating when exposed to these compounds is sufficient to warrant their use in the treatment of such serious, heretofore untreatable, and often fatal diseases, such as cancer. After elucidation of the mode of action of these drugs and a determination of their safety, they may serve additionally as effective agents in the relief of hypertension and pain.

What is claimed:

1. A compound of the formula

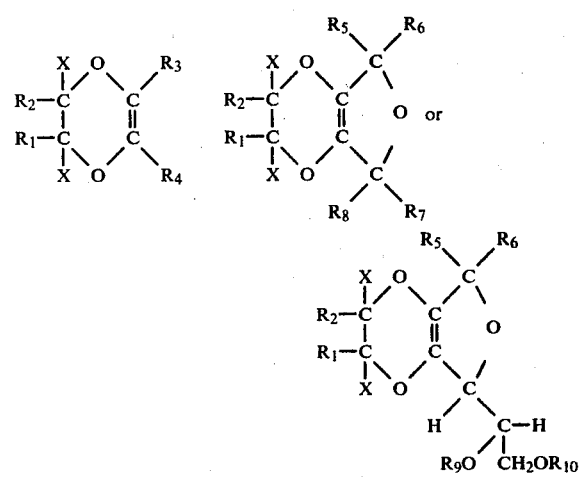

wherein $R_1$ and $R_2$ are selected from the group consisting of hydrogen, lower alkyl, phenyl or phenyl loweralkyl, wherein $R_3$ through $R_{10}$ are selected from the group consisting of hydrogen, lower alkyl and phenyl, wherein $R_5$ and $R_6$ together may form =O, and wherein X is hydroxy.

2. A compound of claim 1, wherein the compound is of the formula

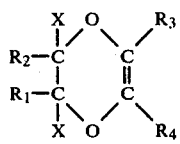

wherein $R_1$ and $R_2$ are selected from the group consisting of hydrogen, lower alkyl, phenyl and phenyl loweralkyl, wherein $R_3$ and $R_4$ are selected from the group consisting of hydrogen, lower alkyl, and phenyl, and wherein X is hydroxy.

3. A compound of claim 1, wherein the compound is of the formula

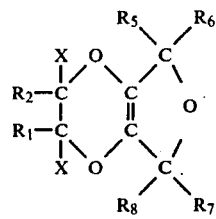

wherein $R_1$ and $R_2$ are selected from the group consisting of hydrogen, lower alkyl, phenyl and phenyl loweralkyl, wherein $R_5$ through $R_8$ are selected from the group consisting of hydrogen, lower alkyl and phenyl, wherein $R_5$ and $R_6$ together may form =O, and wherein X is hydroxy.

4. A compound of claim 1, wherein the compound is of the formula

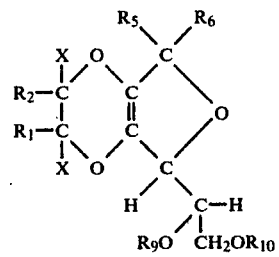

wherein $R_1$ and $R_2$ are selected from the group consisting of hydrogen, lower alkyl, phenyl and phenyl loweralkyl, wherein $R_5$, $R_6$, $R_9$ and $R_{10}$ are selected from the group consisting of hydrogen, lower alkyl and phenyl, wherein $R_5$ and $R_6$ may together form =O, and wherein X is hydroxy.

5. An analgesic composition comprising an effective amount of a compound of claim 1 for treating pain and a pharmaceutical carrier therefore.

6. A hypotensive composition comprising an effective amount of a compound of claim 1 for treating hypertension and a pharmaceutical carrier therefore.

7. A composition for use in the treatment of pain or hypertension comprising a compound of claim 1 dissolved in about 10 to 10,000 weight percent, based on the total weight of said compound, of 0.9 percent saline.

8. A composition for use in the treatment of pain or hypertension comprising a compound of claim 1 dissolved in about 10 to 10,000 weight percent, based on the total weight of said compound, of water.

9. A method for treating pain or hypertension in humans and animals comprising intravenous injection of a composition of claim 7.

10. A method for treating pain or hypertension in humans and animals comprising intraperitoneal injection of a composition of claim 8.

* * * * *

UNITED STATES PATENT AND TRADEMARK OFFICE
CERTIFICATE OF CORRECTION

PATENT NO. : 4,238,500
DATED : December 9, 1980
INVENTOR(S) : Albert Szent-Gyorgi and Gabor B. Fodor It is certified that error appears in the above-identified patent and that said Letters Patent are hereby corrected as shown below:

In column 3, line 21; insert -- and a hydrogen is attached to the carbon connected to -OH and $R_4$, -- after "A is =O" and before ", wherein $R_3$ and $R_4$ ... or".

In column 10, line 31; "$10^6$" should read -- 0.9 to 0.4 --.

Signed and Sealed this

Seventeenth Day of August 1982

[SEAL]

Attest:

Attesting Officer

GERALD J. MOSSINGHOFF
Commissioner of Patents and Trademarks